United States Patent [19]
Caruso et al.

[11] Patent Number: 5,957,869
[45] Date of Patent: Sep. 28, 1999

[54] APPARATUS AND METHOD FOR MEASURING ANATOMICAL ORTHOPEDIC JOINT LAXITY

[76] Inventors: Steven A. Caruso, 53 Cranford St., Staten Island, N.Y. 10308; Steven C. Sheskier, 235 Warren St., Brooklyn, N.Y. 11201

[21] Appl. No.: 08/517,166

[22] Filed: Aug. 21, 1995

[51] Int. Cl.⁶ .................................................. A61B 5/00
[52] U.S. Cl. .................................... 600/592; 600/595
[58] Field of Search .................................. 128/774, 779, 128/782; 33/511, 512, 763, 780

[56] References Cited

U.S. PATENT DOCUMENTS

| | | | |
|---|---|---|---|
| 4,323,080 | 4/1982 | Melhart et al. | 128/782 |
| 4,583,554 | 4/1986 | Mittelman et al. | 128/782 |
| 4,583,555 | 4/1986 | Makom et al. | 128/782 |
| 4,869,265 | 9/1989 | McEwen | 128/774 |
| 4,969,471 | 11/1990 | Daniel et al. | 128/782 |
| 5,335,674 | 8/1994 | Siegler | 128/782 |
| 5,402,800 | 4/1995 | Hollis | 128/779 |
| 5,435,321 | 7/1995 | McMillen et al. | 128/782 |
| 5,471,996 | 12/1995 | Boatright et al. | 128/774 |

OTHER PUBLICATIONS

"Wrist and Shoulder Motion Analyzer", Research Disclosure Nov. 1981 Little et al. pp. 404–405.

Primary Examiner—Max Hindenburg

[57] ABSTRACT

An improved apparatus and method are provided for force and distance indication readings on the prior art MEDmetrics KT 1000™ which eliminate the need for an observer to vigilantly scrutinize the analog distance indicator and which indicate the force used to produce a given distance of travel, with both the force and distance having maximum-read indicators. In addition, a removable receptacle is provided for adapting the prior art KT 1000™ for use in measuring ankle joint laxity. A method of reliably and accurately measuring ankle joint laxity is provided using the improved KT 1000™ device of the present invention.

31 Claims, 9 Drawing Sheets

APPARATUS AND METHOD FOR MEASURING ANATOMICAL ORTHOPEDIC JOINT LAXITY

BACKGROUND OF THE INVENTION

Ankle sprains are the most common injury in sports; the lateral ligament complex of the ankle is most often injured, and approximately one-quarter of all reported sports injuries occur in the foot, among which about one-half are sprains. In addition, ankle sprains account for 10% to 15% of all time lost to injuries in football on the professional, college, and high school levels, with the average player losing five weeks. Ankle ligament injury is also the most common injury in modern and classical dance.

Current methods of determining degree of ankle joint instability, i.e., ankle joint laxity include a stress X-Ray technique of the Talar Tilt. The disadvantages include the time consumed in producing and reading an X-Ray, the relatively high cost, the complexity and the exposure of the patient to X-Radiation.

The manual anterior drawer test comprises a trained person—orthopedic surgeon or other medical professional, pulling upon the suspect ankle to note laxity in the ankle ligaments. Here again, the disadvantages are unreliability and variability within and between doctors and patients.

The present invention provides a method and an improved apparatus for quick, reliable, reproducible, low-cost and risk-free ankle joint laxity measurement which is also very low in variability both intra- and inter-observer.

Reliable orthopedic joint laxity measurement is an important component of orthopedic injury diagnosis, particularly for knee and ankle joints and particularly because knee and ankle joints are frequently injured by people engaging in sports. An orthopedic surgeon who evaluated knee injury prior to the present invention typically may have used a prior art device known as a KNEE LIGAMENT ARTHROMETER® manufactured and sold by MEDmetric Corporation, 4901 Morena Boulevard, Suite 322, San Diego, Calif. 92117, and protected by U.S. Pat. No. 4,583,555. The KNEE LIGAMENT ARTHROMETER® in common use is known as the Model KT 1000™.

The KT 1000™ is the prior art upon which the present invention is an improvement on both the apparatus and the method of use.

The MEDmetric Corporation teaches that its KT 1000™ is to be used for measuring and assessing the integrity of only the ligaments in the knee of a patient being examined. MEDmetric teaches away from the present invention in that the present invention embodies a method of use of the KT 1000™ for ankle laxity measurement and is thus specifically disapproved taught away from by MEDmetric.

While MEDmetric teaches use of its KT 1000™ only for the knee, the present invention teaches use of the KT 1000, with appropriate novel modifications as herein presented and described, for use in measuring the laxity in the ankle joint.

The ankle joint, like the knee joint, is a point of frequent injury, and in particular, sprained and twisted ankles and ankles with more serious ligament injuries need diagnosis as often, if not more often, than injured knee joints.

Thus, the novel method of use of the modified KT 1000™ represents not only novel apparatus modification to the KT 1000™, not only a novel method of using the modified KT 1000™, but also a greatly expanded use for the modified KT 1000™ in that ankle injuries, as a new category of injury, will be added to the utility of the newly-modified KT 1000™.

In so doing, the present invention addresses a long-felt need in the art of orthopedic diagnosis of ankle joint injury, namely, to standardize and to make quick, convenient and most important, reliable, the assessment and diagnosis of injury to the ankle joint. This is especially important in view of the large number of ankle-joint sports injuries which are currently being treated.

The type of injury for which MEDmetric teaches that its KT 1000™ is useful is in diagnosis of injury to the knee in which the cruciate ligament(s) is (are) injured—by tearing, hyperextending, or otherwise. Cruciate ligaments are structures which are specific to the knee.

Injury to the cruciate ligaments often manifests itself in the laxity of the cruciate ligaments, which laxity, in turn, results in the tibial bone having more relative translational movement ability than would be available to the tibial bone in a normal healthy knee.

Because the tibial bone is able to wobble in a knee where the cruciate ligaments are compromised, a knee with injury to the cruciate ligaments may be termed unstable by an orthopedic surgeon. The person afflicted with this kind of cruciate ligament injury is not going to be able to rely on the firm placement of the tibial bone.

The injured person may thus experience a tibial wobble characterized by an inadvertent, unwanted and uncontrolled mis-alignment of the tibial bone in relation to the knee while the knee and leg are under stress, as during a standing, walking or sports-playing activity. The misalignment, resulting from the wobble, predisposes the person with the injured knee to further injury and/or re-injury.

The KT 1000™ is an instrument specifically designed for use by an orthopedic doctor to measure the degree to which knee ligaments are lax, thus permitting at least the possibility of a potentially dangerous tibial wobble. If the knee ligaments are more lax than they should be, the tibia will have the ability to travel anteriorly or posteriorly when an examining doctor applies force in the respective anterior or posterior direction to the calf of the patient, since the tibial bone is in the calf.

If the tibia is permitted to travel more than a healthy distance in an anterior or a posterior direction, knee ligament laxity, and thus knee injury, is indicated by the fact of the anterior or posterior movement.

Diagnostic measurement of ankle joint laxity is an important part of the novelty of the method of use of the present invention. In the ankle joint, injury to and laxity of the following ligaments, in the following order is involved: (1) the anterior talofibular ligament; (2) the calcaneofibular ligament; and (3) the posterior talofibular ligament. It is in that order that the ligaments of the ankle fail under the stress of an injury such as an ankle sprain. The least serious ankle injury involves compromise only to the first, anterior talar fibula ligament. Progressing, injuries of increasing severity will compromise the calcaneofibular ligament second; and finally, the posterior talofibular ligament will be compromised in the most severe ankle sprain.

With any or all of the foregoing ankle ligaments compromised, the ankle joint will be permitted forward, or anterior movement. The more lax the ligaments, the greater the anterior movement will be noted by the examining doctor. It is reliability, reproducibility, comfort and convenience to ankle joint laxity measurement that the method of the present invention provides.

Because of the configuration of the fibula and the calcaneous bones, forward or anterior motion of the ankle joint will depend upon the joint being adjusted so that the foot is slightly bent-down. Orthopedically this condition is known as joint flexion. When the foot bends downward from a neutral position, the flexion is called plantar flexion. Thus, with an optimal degree of plantar flexion, experimentally found to be about 10° from the neutral position, ankle joint laxity can be reliably and accurately measured according to the present invention.

The usefulness of a machine, as compared to an examination performed by a doctor, orthopedist or surgeon using the hands alone is that a machine is capable of giving reliable indications of both force applied and the differential displacement of the joint in the case of knee joint examination. Thus, an important part of the problem solved by the novelty of the present invention is the introduction of instrument reliability and reproducibility to the diagnosis of ankle joint injury and the measurement of ankle joint laxity.

While The KT 1000™ machine represents an effort to standardize diagnosis of cruciate ligament knee injury and is thus advantageous over the less reliable subjectivity of non-instrumented diagnosis, the KT 1000™ also has disadvantages. To begin with, the KT 1000™ is designed for contact upon and measurement of the knee joint only.

Consequently, the KT 1000™ has structures for contacting the anatomy of a patient being examined which are specifically named for the body parts which are to be contacted. The KT 1000™ has two tabular anatomical reference pads, which MEDmetrics respectively calls the patella sensor pad and the tibial sensor pad, based upon the fact that when the KT 1000™ is put in use as taught by MEDmetric, the patella sensor pad is placed in contact with the patient's knee (patella), and the tibial sensor pad is placed in contact with the anterior aspect of the proximal tibia, in other words, on the front (anterior) portion of the lower leg below the patient's knee.

It is a disadvantage to name the anatomical reference pads by the specific anatomical structure to which they are applied because when the modified KT 1000™ is used in the present invention, the ankle, and not the knee is measured for laxity and the anatomical structures are different in the ankle than in the knee. Therefore, the present invention calls the sensor pads anatomical reference pads.

In the present invention, as well as in the prior-art KT 1000™, the sensor pads are capable of moving laterally in relationship to each other. The prior art KT 1000™ measures relative translational movement of the tibia in the anterior and/or in the posterior direction. The more movement, the greater the degree of laxity of the knee joint and thus the greater the severity of the injury being diagnosed.

Such relative translational movement is produced in the prior art KT 1000™ when the examining doctor applies differential force to the patient's tibia by exerting a pulling force in an anterior direction or a pushing force in the posterior direction on the handle provided for that purpose in the prior art KT 1000™. The patient's tibia, if it can move anteriorly, will cause anterior directional movement in the tibial sensor pad of the KT undergo posterior translational movement.

Thus, the tibial sensor pad will experience relative anterior movement or relative posterior movement of a certain number of millimeters relative to the patella sensor pad. The greater the anterior or posterior distance traveled, the greater the knee joint laxity.

The examining doctor's concern in using the prior art KT 1000™ is to ensure that the KT 1000™ is properly positioned and aligned on the knee of the patient, and to observe and record how much anterior-direction force or posterior-direction force is used and how much instability exists in the knee joint as determined by the number of millimeters of anterior or posterior travel, also called translational movement, is available to the tibial bone.

Unfortunately, other major disadvantages exist in the prior art KT 1000™ surrounding the crucial functions of observation and data recordation by the examining doctor. The prior art KT 1000™ is provided with a dial-type analog indicator for showing the relative distance of reference pad travel.

The prior art KT 1000™ analog dial is marked in increments representing millimeters of pad travel, and a rotary indicator turns clockwise or counterclockwise to indicate the direction of relative pad movement, with the magnitude of distance indicated by the arc traveled by the dial indicator, which sweeps out a given number of millimeter increments. The prior art analog distance indicator is zero-adjustable.

But the disadvantage in this analog dial-type distance indicator is the fact that the examining doctor must keep his or her eyes vigilantly upon the dial to note how much movement, i.e., how many millimeters, are traveled by the reference pads, and thus by the tibia under examination. When the examining doctor releases his or her anterior-direction pressure upon the handle of the prior art KT 1000™, the patient's knee joint immediately resumes its pre-examination position.

Unfortunately, when the patient's knee resumes its position, so does the analog distance indicator on the prior art KT 1000™, and if the examining doctor failed to note the very brief extent of the arc swept by the analog indicator, the doctor will have to repeat the pressure test.

A further disadvantage of the prior art KT 1000™ is the fact that the examining doctor may apply pressure in an anterior direction by pulling the handle of the KT 1000™ provided for that purpose—but the doctor has no way to know how much pulling pressure is being applied until a force of 15 pounds, or 67 Newtons (N) is achieved, at which time, the prior art KT 1000™ sounds a horn. Upon further application of 20 pounds (89 N) of anterior direction force, a second, different tone is sounded by the KT 1000™ horn to alert the examining doctor to the amount of force being applied.

Not only is there no available measure of smooth and continuous application of anterior force, against which knee joint laxity may be measured, but also, the sounding of the horn is likely to frighten the patient. And there is no way for the examining doctor to know how far above 20 pounds of anterior force he or she may have applied, and further there is no way for the doctor to know how much force was applied above 15 pounds but below 20 pounds, since the 15-pound horn will sound at any applied force level at or above 15 pounds but below 20 pounds.

Indeed, in product literature, MEDmetrics president K. R. Watkins states that "[t]here are several factors other than instrument accuracy which may affect displacement measurement. Physiological variation, tester technique, conditioning of patient, pretesting activity and apprehension of the patient are a few of these." [emphasis added] Watkins, K. R., introductory remark dated June, 1990, San Diego, Calif., included with KT 1000™.

The product literature referred to comprises reprints of several studies, which product literature is collectively called Knee Stability Measurement Using the KT 1000™ Knee Ligament Arthrometer® A collection of studies printed in journals compiled by MEDmetric Corporations, manufacturers of orthopedic instrumentation including the KT 1000™, and dated San Diego, Calif., June, 1990.

It would be a great advantage to be able to note not only how much anterior joint movement is present, and thus how lax the joint is, but also to know how much force was needed to produce the anterior joint movement. If, for example, two patients show anterior movements of, say, 4 millimeters, it may also help the examining doctor to know whether 3 pounds, 5 pounds, 10 pounds, 15 or 20 pounds of anterior direction force were required to produce the 4 millimeter movement.

If less force were required to produce the same movement, then both force and movement should be taken into account in assessing joint laxity. The same movement produced by less force indicates a more severely injured and thus less stable joint—since it is ultimately the patient who will be applying the pressure of normal or rehabilitative effort to the joint being diagnosed.

The present invention solves the afore-described problems of the reversible analog dial-type distance indicator requiring intense observer vigilance, the problem of the inability to note or to measure force other than at 15- and 20-pound discrete levels, and the problem of patient fright by the prior art KT 1000™ force indicator being provided in the form of an audible horn with different tones for the 15 and 20-pound levels. Such an audible horn is a natural patient fright-producer, and is thus a severe drawback of the prior art KT 1000™.

OBJECTS OF THE INVENTION

To overcome the disadvantages of the prior art, it is an object of the present invention to provide a method of using an improved KT 1000™ to measure ankle joint laxity.

It is a further object of the present invention to eliminate the need for observer vigilance on an analog measure of relative reference pad distance traveled.

It is yet another object of the present invention to eliminate a noisy and frightening audible horn indication of force applied.

It is another object of the invention to provide a maximum-reading indicator for relative distance traveled by anatomical reference pads.

It is still another object of the invention to provide a maximum-read continuous indication of force applied.

It is still another object of the invention to provide an improvement to the KT 1000™ so as to have a calcaneous reference pad in the form of a receptacle.

It is yet another object of the invention to provide a receptacle calcaneous reference pad which is clampable and adjustable.

It is yet another object of the invention to provide a receptacle calcaneous reference pad which is conveniently removable from the prior art KT 1000™ and which further can be conveniently installed and removed for switching between use of the improved KT 1000™ of the present invention for ankle joint and for knee joint measurement.

It is also an object of the present invention to overcome the disadvantages of the prior art.

SUMMARY OF THE INVENTION

In keeping with the aforesaid objects of the invention and others which may become apparent, the present invention modifies the prior art KT 1000™ with novel improvements as follows. First, the analog distance indicator of the prior art may remain as an analog dial-type indicator which is zero-adjustable and has radially disposed clock-like incremental indicia of arc travel representing millimeters of reference pad travel. However, the novelty of the present improvement lies in the modification of the indicator to be a maximum-read indicator.

In other words, once it is zero adjusted, the analog indicator of the present improvement moves only in the direction indicative of pad travel—and does not reverse its movement when the pads return to their original positions. The indicator of the present invention functions the same way that a medical thermometer functions—by reaching a maximum reading and remaining in that condition until reset.

The advantage gained by a maximum read pad travel distance indicator is that the examining doctor no longer has to apply concentrated vigilance in observing the distance travel indicator—it will now with the present invention automatically maximum-read. The examining doctor will be free to observe the patient and the conditions of the examination without undue or special focus on observing the prior art KT 1000™ which very briefly displays numerical value of an indicator.

While the preferred embodiment of the present invention employs the above-described maximum-read analog distance indicator, a non-preferred embodiment of the present invention provides for a digital display of distance traveled.

As to solving the problem of the prior art KT 1000™ force indicator having an audible horn, the preferred embodiment of the present invention employs a plurality of indicator lights. The indicator lights may be any suitable design or type, such as LEDs, and may be of a single color or a variety of colors where color-coded force magnitude indication is desired.

In the preferred embodiment of the present invention, force is indicated by the sequential illumination of a series of indicator lights, in such a manner that each illuminated indicator light represents a given number of pounds of force. For example, each indicator light could represent 3 pounds of force, so that when 4 such lights are illuminated, 12 pounds of force are indicated. As with the maximum-read analog distance indicator, the indicator lamps showing applied force are also maximum-read indicators, and will remain illuminated until the force indicator is reset. Current for indicator lamp illumination will be provided by a suitable battery.

It is also possible to provide for a series of indicator lights which illuminate sequentially to indicate a narrow range of increasing force values, as, for example a series of indicator lights which do not light up until, say, 15 pounds of force is exerted. But, when 15 pounds of force is reached, the indicator light illuinate sequentially as each 1-pound increment of force is applied. Thus, between the application of 15 pounds and 20 pounds of force, there might be six indicator lights, each illuminating when a successive individual pound of force is exerted.

In a non-preferred embodiment of the present invention, the magnitude of force applied may be indicated by indicator lights of different colors, singly illuminated or in combinations. For example, a blue indicator light could indicate 3 pounds of applied force, a green light could indicate 6 pounds, and so forth.

Alternatively, and also non-preferred, is an embodiment of the present invention in which printed indicia upon the improved device of the present invention may indicate a given force level, as where, for example, a plurality of indicator lights have imprinted adjacent to them, respectively, 3 pounds, 6 pounds, 9 pounds, and so forth, so that when a respective indicator lamp is illuminated, the indication is the number of pounds of force imprinted adjacent to the illuminated lamp.

In yet another non-preferred embodiment of the present invention, applied force may be displayed digitally. Such a digital display of distance traveled in relation to force applied is very common and well known in such fields of art as weight measurement in both commercial and laboratory settings.

Having solved the problems of the prior art KT 1000™ for the knee-joint measurement for which it was designed, it is a further aspect of novelty of the present invention to provide a method of using the prior art KT 1000™ in a way for which it was not designed and for which its manufacturer teaches that it is non-useful—namely, to describe and to claim a method of using the improved KT 1000™ to measure the laxity not of the knee joint, but of the ankle joint.

Using the improved KT 1000™ for ankle joint laxity measurement may be accomplished as follows: the anatomical reference pad which the KT 1000™ manufacturer calls the patella pad will be used to contact the heel of the patient being examined. Within the heel is the calcaneous bone, and thus the reference pad in the improvement of the present invention is called the calcaneous pad when the improved device is used for ankle joint diagnosis.

When the patella pad is used as a calcaneous reference pad for ankle measurement, the improved KT 1000™ must be oriented upon the leg of the patient being examined in a manner different from its use in the prior art. In the first place, the use of the KT 1000™ for the knee requires that the device be oriented so that the patella reference pad is located proximally, or nearest to the body of the patient.

However, when the improved KT 1000™ is used for ankle joint measurement, the patella pad, now called the calcaneous pad in use for ankle joint measurement, is oriented 180° opposite to its orientation for knee joint measurement. This means that the patella pad, now called the calcaneous reference pad, is located distally, or furthest from the body of the patient. Simply put, in order to use the improved KT 1000™ to measure ankle joint laxity, it is necessary to turn it around 180° from its position used to measure knee joint laxity. The patient must be in a prone position.

Furthermore, the novel apparatus modification of the present invention includes a substantially cube-shaped calcaneous reference pad comprising a receptacle for grasping the patient's heel. With the patient's heel thus immobilized, the device of the present invention is sufficiently positionally stable to produce reliable and reproducible results without wobbling in place upon the calcaneous of the patient.

The calcaneous pad receptacle may be comprised of a plurality of facets; and the receptacle further comprises a foot-stop plate for use in applying to the device to the foot of a patient adjacent to the calcaneous bone.

The receptacle may comprise a concave shape having internal facets of soft material such as foam rubber for comfortably grasping the heel of the patient. The concave internal cavity of the receptacle preferably has five facets for contacting the heel of the patient being examined so as to form a cup-like internal cavity.

The means for convenient and suitable application to and removal from the reference pads comprises a channel disposed on the receptacle for slidable friction-fitting on the reference pads. The receptacle slides onto and off from the KT1000 patella reference pad, here called the calcaneous pad.

With the receptacle thus installed, the Prior Art KT1000 becomes, by virtue of its combination with the receptacle, a new device for measuring ankle joint laxity.

The calcaneous pad modification of the present invention may be easily installed or removed onto or from the KT 1000™ by a friction-fit sliding channel arrangement.

In addition, the walls of the cube-like heel receptacle calcaneous pad in the preferred embodiment are capable of squeezing together in clamp-like fashion by a threaded shaft hinge arrangement penetrating through the pad and drawing the cube wing walls toward each other. The wing walls, thus hinged and positionally adjustable upon the heel of a patient, are clamped in place as desired by means of wing nuts disposed on a portion of the threaded hinge shaft which extends outward from the receptacle so that when the wing walls are in a desired position they may be clamped by the friction grasp provided by tightening of the wing nuts. In this manner the calcaneous pad is capable of grasping the heel of the patient and thereby the KT 1000™ device is stabilized in place in preparation for measurement of ankle joint laxity.

The calcaneous pad receptacle may be provided with an interior grasping surface of hard rubber or other suitable non-slippery material, such as a relatively hard elastomer which will not permit the patient's foot to move appreciably.

In addition, when the prior art KT 1000™ is used to measure the knee joint laxity, the device is placed on and in contact with the anterior portion of the patient's calf. However, to use the improved KT 1000™ of the present invention, the device is placed on and in contact with the posterior portion of the patient's calf.

The prior art KT 1000™ as well as the improved KT 1000™ of the present invention is conveniently and suitably affixed in position by means of hook-and-loop straps.

With the improved KT 1000™ affixed in position for ankle joint measurement, the calcaneous reference pad is in contact with the heel of the patient and the other reference pad is in contact with the posterior calf of the patient, adjacent to the Achilles tendon. While this area of the patient's anatomy is somewhat soft, and might otherwise be considered subject to allow relative movement due to the absence of a firm anatomical reference structure, it has been found in practice with the method of using the improved KT 1000™ of the present invention that, indeed, it is not only possible to obtain reliable ankle joint laxity measurements, but that such measurements are easy and convenient as well.

With the improved KT 1000™ of the present invention in place on the patient, the examining doctor measures the laxity of the ankle joint by applying force in an anterior or in a posterior direction. As with the knee, the laxity of the joint in a posterior movement indicates the laxity of certain ligaments, while anterior laxity indicates the compromise of different ligaments.

In this novel method using the prior art KT 1000™ the present invention has solved the recognized problem in orthopedic diagnosis of how to reliably, accurately, reproducibly, conveniently and comfortably measure the laxity of an injured ankle joint.

A further apparatus improvement made by the present invention over and above the prior art apparatus of the KT 1000™ is an anatomical reference pad which comprises a receptacle.

The prior art KT 1000™ has two reference pads, as noted above, a patella reference pad and a tibial reference pad. Both of these pads in the prior art KT 1000™ are substantially flat and tabular. They are placed in contact with the patient, but they do not conform to the contours of the patient's anatomy at the point where they contact the skin. To provide a better contour fit as an improvement, and to make ankle joint laxity measurement yet more reliable, a patient heel receptacle has been added.

As a novel improvement over the prior art KT 1000™ the present invention provides a molded, form-fitting heel receptacle which comprises one of the reference pads—specifically, the calcaneous reference pad for application to the patient's heel when ankle joint laxity is being measured.

In the preferred embodiment of the present improved KT 1000™ invention, the heel-receptacle calcaneous reference pad is conveniently removable, thus comprising an adapter for the device. The heel receptacle adapter in place, ankle joint laxity may be easily measured. And with the adapter removed, knee joint laxity may be easily measured.

The heel receptacle-adapter is a substantially cube-like structure having appropriate openings for accepting the foot and heel of the patient whose ankle laxity is being measured, and the receptacle is further provided with an attachment channel for slidable friction-fitting attachment onto the existing planar patella reference pad of the prior art KT 1000™.

In a non-preferred embodiment, the heel receptacle is provided as a built-in, non-removable reference pad, and the device is then useable only for measurement of ankle joint laxity.

In a further improvement, the heel receptacle may be provided with a foot-bottom stop member so as to provide not only a receptacle for the heel of the patient, but also a flat bottom for the receptacle so as to conveniently and reliably locate the receptacle by contact with not only the patient's heel, but also with the bottom of the patient's foot for the above-described process of measuring ankle joint laxity.

To summarize the method of using the present invention to measure the ankle joint laxity in a patient being medically examined, the steps of the method comprise the following:

a. affixing the receptacle to the heel of the patient lying in the prone position on the ankle to be measured for joint laxity;

b. applying a KT 1000™ reference pad to the patient by bringing it in contact with the posterior portion of the patient's calf, so that the reference pad is adjacent to and capable of pressing upon the patient's Achilles tendon, the reference pad so affixed being a tibial reference pad since in position it is disposed adjacent to the patient's tibial bone; and c. applying force to the respective reference pad and the calcaneous receptacle so as to produce lateral movement therebetween;

d. observing and recording the indication of the amount of lateral distance traveled by the reference pad and the calcaneous receptacle relative to each other; and e. observing and recording the indication of the amount of force applied to produce the relative distance traveled by the reference pad and calcaneous receptacle relative to each other as indicated by the force indicia; and f. repeating the foregoing steps on the patient's other foot, ankle and leg for reference comparison; and g. repeating the foregoing sequence to observe and record inherent intra-patient variability.

Clinical testing by the inventors of the present invention using the prior art KT 1000™ for ankle joint laxity measurement has proved quite successful, despite the manufacturer's indications that ankle joint measurement may be ineffective or impossible with the KT 1000™.

Ten human cadavers were obtained shortly after death. Although not statistically significant, five right ankles and five left ankles were used for the clinical test. All possible specimens were tested for range of motion using a goniometer. Ankles displaying acceptable ranges of motion [ROMs] particularly with regard to plantar flexion were tested.

In the test the cadaver was placed in a prone position so that the ankle and anterior tibia could be placed in a specially designed testing platform, necessitated by the fact that cadavers could not assist in their own testing as would a live patient.

The testing platform allowed for ankle joint neutral position testing and for testing the ankle with plantar flexion of 30° The cadaver specimen was kept immobile and the prior art KT 1000™ was applied to the cadaver as described above in the method of use for ankle joint laxity testing. The patella reference pad—here used as a calcaneous pad—was applied and contacted to the heel of the cadaver, which is adjacent to the calcaneous bone within the heel.

Each specimen was tested for ankle joint laxity using the prior art KT 1000™ with the above described method by two researchers taken from a pool of three researchers.

Each of the two researchers conducted three trials under a variety of variable conditions, including plantarflexed angle of 30° and a neutral ankle flexion angle of zero degrees. Force magnitude used in the prior art KT 1000™ was at the 20-pound level as indicated by the audible horn of the prior art KT 1000™. In addition, comparison trials were made using maximum manual force in place of the prior art KT 1000™.

The foregoing test procedure was then repeated, after transecting the anterior talofibular ligament [ATFL] and again after transecting the calcaneofibular ligament [CFL].

After all data on relative translational distance movement [i.e., a measurement of ankle joint laxity] were acquired and recorded for each ankle, a complete dissection of the joint was performed in order to examine the specimen for any conditions such as arthritis which might have caused data to be rejected.

The results of the aforedescribed trials were as follows:

It was found that relative displacement of the ankle joint increased upon each subsequent ligament transection (Neutral<ATFL Cut<ATFL&CFL Cut). It was also found that trial using manual maximum force testing produced greater displacements than standardized 20 pound force as indicated by the audible indicator horn of the prior art KT 1000™.

It was further found that testing with the ankle at 30° plantarflexion produced greater displacements than testing with the ankle at the neutral position (0°).

After adjustment for all other factors, no effect on ankle joint displacement was attributable to the observer ($F=0.80$, $p=0.45$). After adjustment for all other factors, the ankle joint displacement within each subject did not differ significantly between trials. A table of the overall results is as follows:

| RESULTS TABLE | NORMAL UNCUT mm distance | ATFL TRANSECTED mm distance | ATFL & CFL TRANSECTED mm distance |
| --- | --- | --- | --- |
| 20 LB FORCE Neutral Angle | 3.79 (+/−.97) | 7.63 (+/−2.20) | 9.14 (+/−2.38) |
| 20 LB FORCE 30° Angle | 3.51 (+/−1.04) | 7.31 (+/−2.91) | 9.03 (+/−2.87) |

-continued

| RESULTS TABLE | NORMAL UNCUT mm distance | ATFL TRANSECTED mm distance | ATFL & CFL TRANSECTED mm distance |
| --- | --- | --- | --- |
| MANUAL MAXIMUM Neutral Angle | 5.68 (+/−1.11) | 9.82 (+/−2.33) | 11.73 (+/−1.91) |
| MANUAL MAXIMUM 30° Angle | 6.47 (+/−1.41) | 11.80 (+/−3.15) | 14.61 (+/−2.50) |
| OVERALL | 4.86 (+/−1.69) | 9.14 (+/−3.22) | 11.13 (+/−3.34) |

An analysis of the foregoing results of the use of the prior art KT 1000™ for ankle joint laxity measurement demonstrate that the novel method of the present invention using the prior art KT 1000™ alone, without the novel apparatus improvements of the present invention can reliably and reproducibly distinguish between varying ankle ligament conditions, independent of ankle position and amount of force administered.

In addition, the prior art KT 1000™ when used with the novel method of use of the present invention—and used alone, without the novel apparatus improvements of the present invention can reliably and reproducibly distinguish between varying ankle ligament conditions, independent of the person performing the test, thus providing a low degree of intra-observer variability.

From the results table above, it is shown that testing at 30° plantarflexion yielded significantly greater ankle displacements (statistically) than testing at neutral (0°). This is due to the fact that the ankle mortise blocks the talus from significantly moving anteriorly when the ankle is in neutral. Plantarflexion during an anterior draw test allows the talus to slide under the anterior border of the ankle mortise, thus producing less resistance to anterior motion.

It was also found that testing with the manual maximum force procedure produced statistically significant increases in ankle joint displacement, when compared to testing done using the standardized 20-pound force provided by the prior art KT 1000™.

Eleven ankles were actually tested in the above results, but one set of data was discarded due to the post-testing dissection of the specimen, which revealed abnormal ligament arrangements/connections.

A study published after the data was collected for the above-described clinical experiment determined that the optimum angle for anterior draw testing is 10° plantarflexion. The goal of the above experiment was to show that the Anterior Draw Test, embodied by the above described method, data and results could be reliably reproduced using the prior art KT 1000™ regardless of a number of variables. The 30° of plantarflexion used in the above experiment was considered to be the higher end of the expected range of motion of the average ankle joint, and thus produced a high separation of variables.

It is thought that at the optimum angle of 10° of plantarflexion that the above described method will produce ideal results of accuracy reliability and reproducibility.

BRIEF DESCRIPTION OF THE DRAWINGS

The invention can best be understood in conjunction with the drawings, in which

FIG. 1 shows the prior art KT 1000™ having a patella sensor pad, a tibial sensor pad, an analog distance or displacement indicator dial, and a force transmitting handle.

DETAILED DESCRIPTION OF THE DRAWINGS

Further modifications may be made to the present invention without departing from its scope, as noted in the appended claims.

Figure 1:
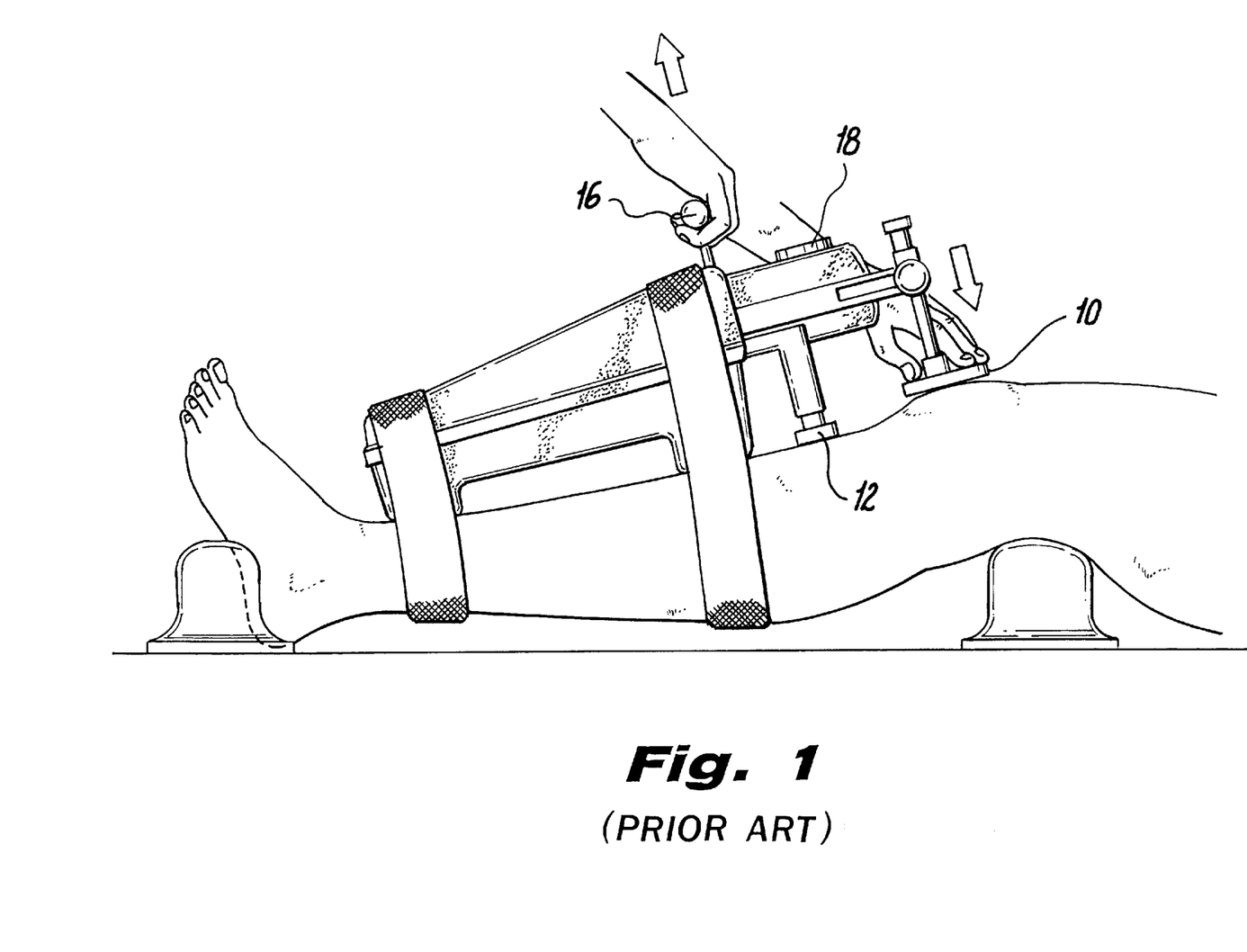
FIG. 1 shows the prior art KT 1000™ in a schematic view, with the KT 1000™ in position for measuring knee joint laxity.

FIG. 1 shows the prior art KT 1000™ having a patella sensor pad 10, a tibial sensor pad 12, an analog distance or displacement indicator dial 18, and a force transmitting handle 16.

Figure 2:
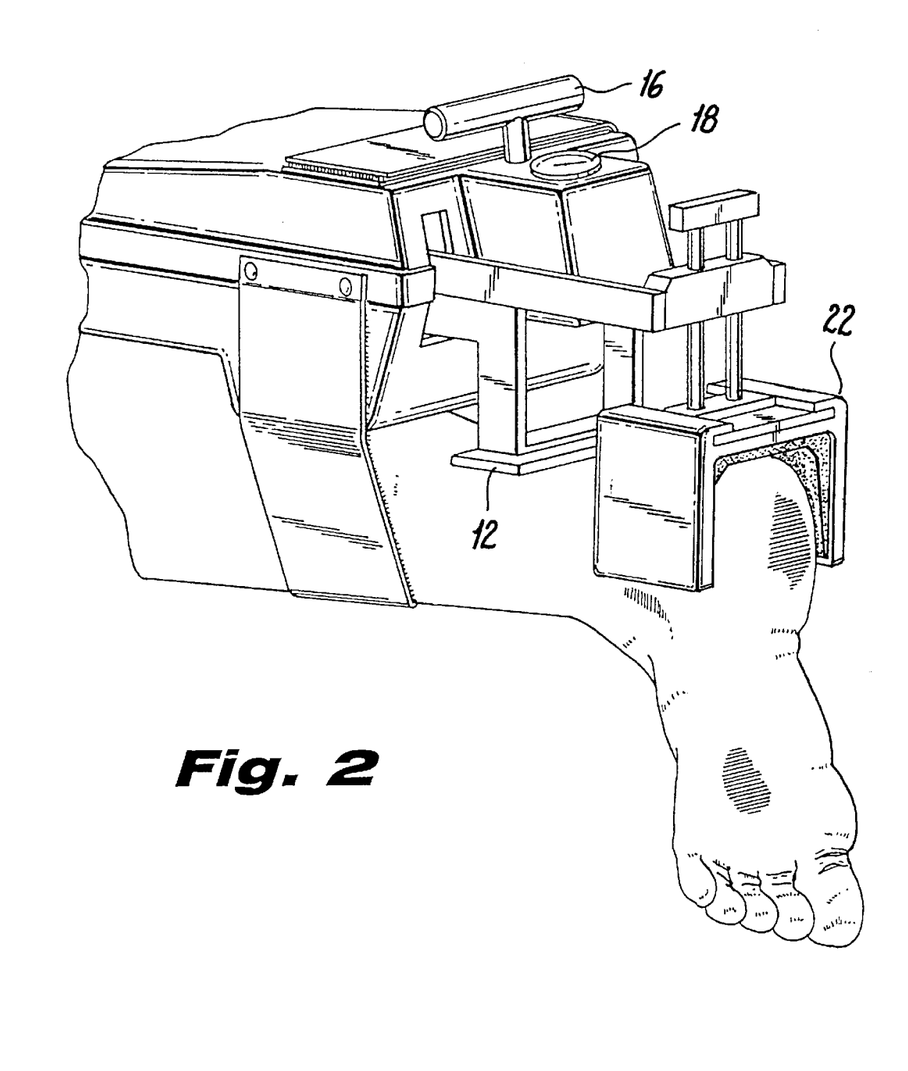
FIG. 2 shows the prior art KT 1000™ in place for measuring ankle joint laxity according to the novel method of the present invention. A calcaneous reference pad is shown in position on the heel of the patient.

FIG. 2 shows a persepctive view of the prior art KT 1000™ with the novel improved calcaneous reference pad heel receptacle adapter 22 in place on the heel.

Figure 3:
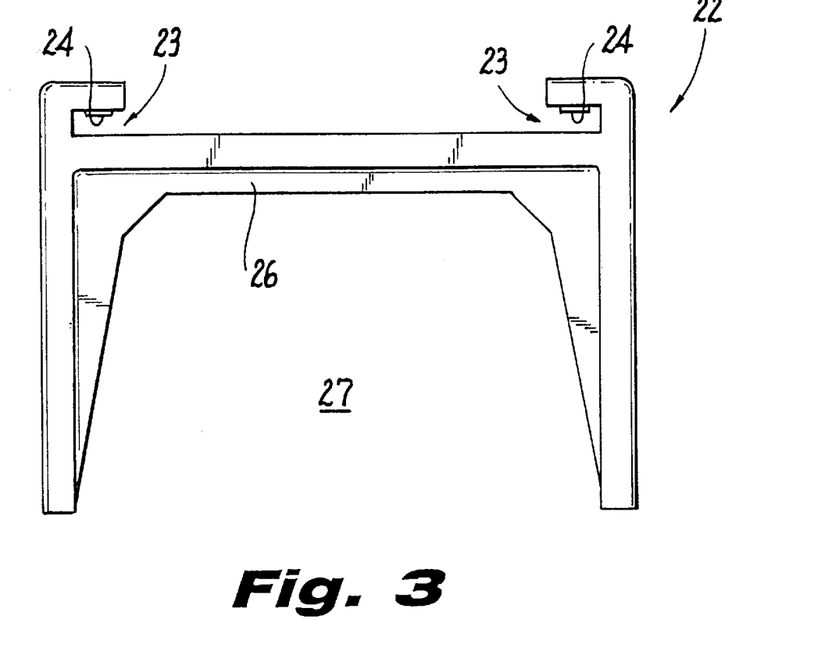
FIG. 3 shows an end view of the heel receptacle adaptor comprising the calcaneous reference pad.

FIG. 3 shows and end view of calcaneous reference pad heel receptacle adapter 22 having attachment channels 23 with friction spring clips 24 for easy and convenient slidable installation and removal from standard planar reference pad 10 provided in the prior art KT 1000™. Non-slippery material 26 for contacting the heel of a patient surrounds substantially concave receptacle area 27.

Figure 4:
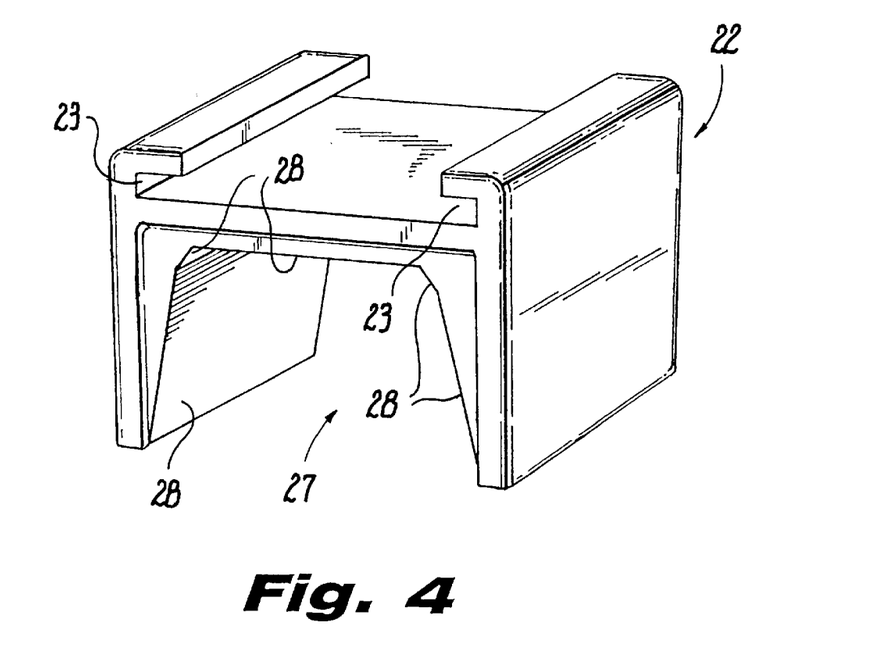
FIG. 4 shows a persepective view of the heel receptacle adaptor shown in FIG. 3.

FIG. 4 shows a perspective view of the heel receptacle adapter 22 shown in FIG. 3 having attachment channels 23 for slidable mounting of receptacle 22 onto calcaneous reference pad 10 of the prior art KT1000. Concave receptacle area 27 is surrounded by non-slippery material 26 for gripping the heel of a patient whose ankle joint laxity is being measured. Concave receptacle area 27 is comprised of planar facets 28 of which there may be five, as shown.

Figure 5:
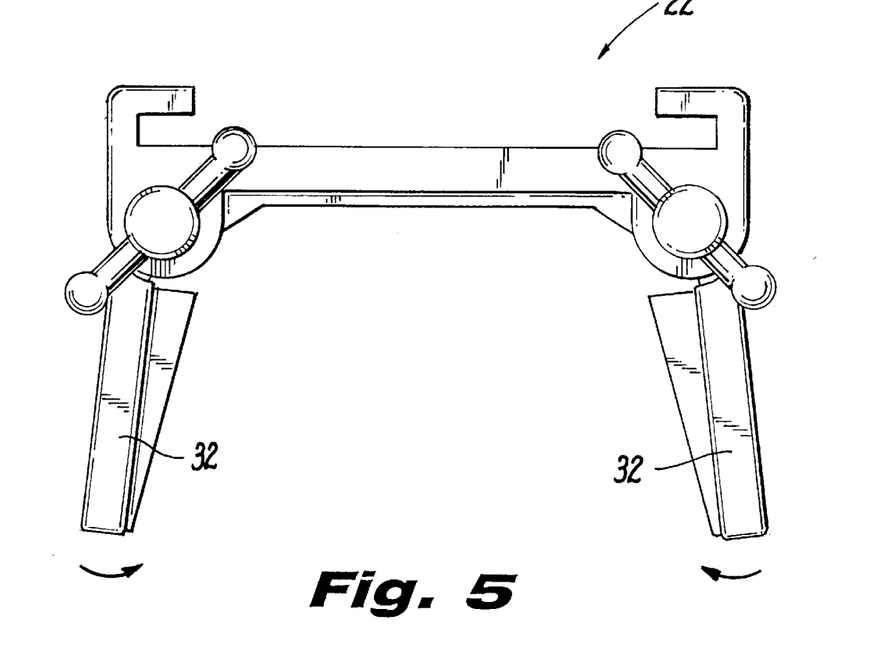
FIG. 5 shows an end view of a heel receptacle adapter having adjustable clamping wing walls.

FIG. 5 shows an end view modification of calcaneous reference pad heel receptacle adapter 22 having clamping wing walls 32 for grasping the heel of the patient.

Figure 6:
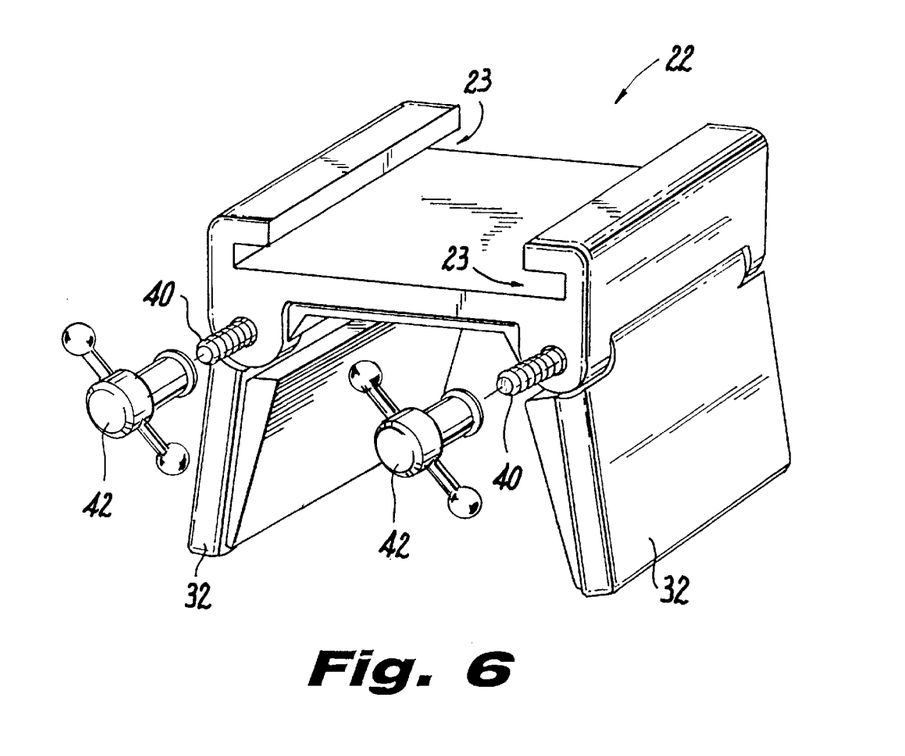
FIG. 6 shows a persepctive view of the adjustable heel receptacle adapter of FIG. 5.

FIG. 6 shows a perspective detail of receptacle 22 as in FIG. 5, having hingedly attached clamping wing walls 32 for adjusting to the size of the heel of a patient whose ankle joint laxity is being measured. Threaded posts 40 comprise hinge pins for wing walls 32. Wing nuts 42 are provided for clamping the wing walls 32 in a clamped position upon the patient. Threaded posts 40 are shown extending beyond the confines of receptacle 22 so as to accept wing nuts 42 thereon.

Figure 7:
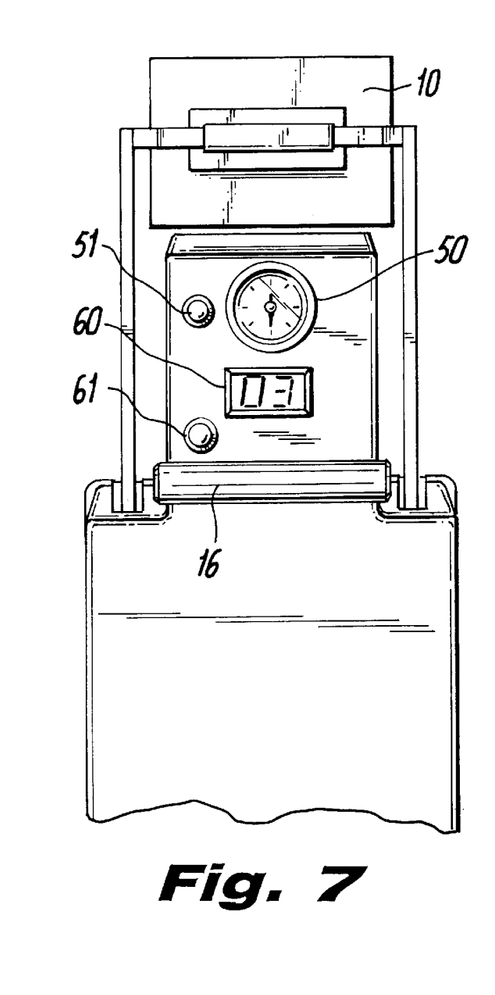
FIG. 7 shows a top view of the Prior Art KT100™ having a novel manually re-settable analog maximum-reading indicator for displaying relative displacement of the reference pads and a manually re-settable digital maximum-reading indicator for displaying user force applied.

FIG. 7 Shows a top view of the Prior Art KT1000™ having novel analog manually re-settable maximum-reading indicator 50 for displaying relative displacement of the reference pads; manual reset push-button 51 allows the user to reset indicator 50 after each reading. Novel digital manually re-settable maximum-reading indicator 60 is shown for displaying force applied by the user; manual reset push-button 61 allows resetting of the force indicator after each reading. Indicators 50 and 60 are in the same general location on the prior art KT1000™ as was occupied by the prior art displacement dial 18 as shown in FIG. 1.

Figure 8:
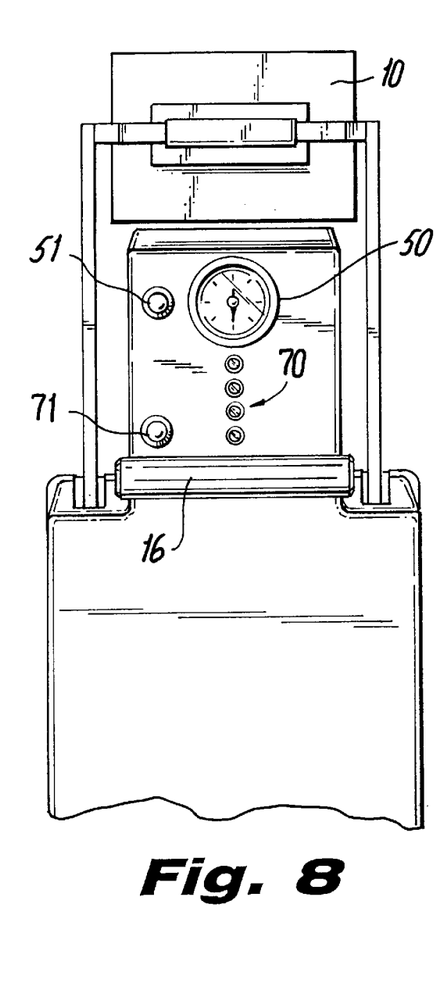
FIG. 8 shows a top view of the Prior Art KT100™ having a novel manually re-settable analog maximum-reading indicator for displaying relative displacement of the reference pads and a manually re-settable plurality of indicator lamps for sequential incremental illumination to display the amount of user force applied.

FIG. 8 shows a top view of the Prior Art KT100™ having a novel manually re-settable analog maximum-reading indicator 50 for displaying relative displacement of the reference pads; manual reset push-button 51 allows the user to reset indicator 50 after each reading. FIG. 8 also shows a manually re-settable plurality of indicator lamps 70 for sequential incremental illumination to display the amount of user force applied. Manual reset push-button 71 permits the user to re-set incremental indicator lamps 70 after each reading. Lamps 70 may be provided in different colors so that only one lamp of a given color is illuminated to indicate force applied. For example, a green lamp might indicate 3 pounds of force, a white lamp 6 pounds of force and a red lamp for example might indicate 20 pounds of force.

Figure 9:
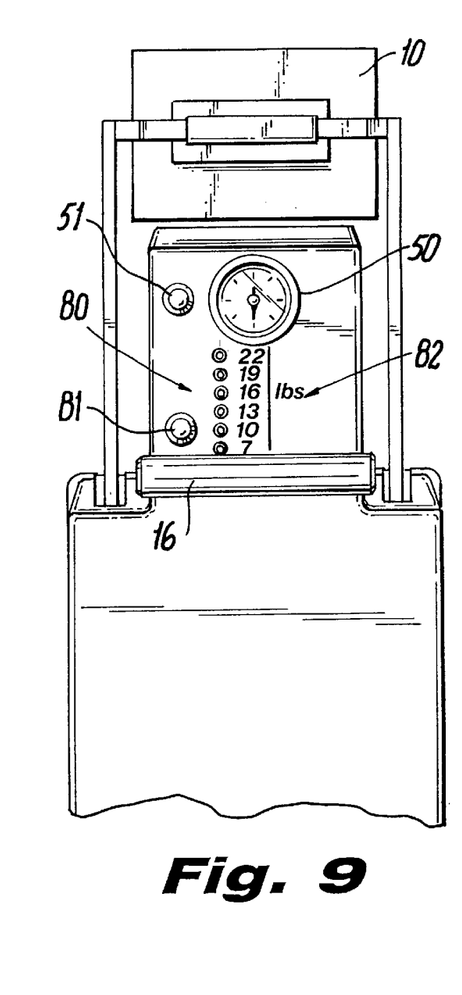
FIG. 9 shows a top view of the Prior Art KT100™ having a novel manually re-settable analog maximum-reading indicator for displaying relative displacement of the reference pads and a manually re-settable plurality of indicator lamps for sequential incremental illumination to display the amount of user force applied where the indicator lamps have indicia adjacent thereto for indicating the amount of user force applied when each sequential lamp is illuminated.

FIG. 9 shows a top view of the Prior Art KT100™ having a novel manually re-settable analog maximum-reading indicator 50 for displaying relative displacement of the reference pads; manual reset push-button 51 allows the user to reset indicator 50 after each reading. FIG. 9 also shows a manually re-settable plurality of indicator lamps 80 for sequential incremental illumination to display the amount of user force applied. Manual reset push-button 81 permits the user to re-set incremental indicator lamps 80 after each reading. Indicator lamps 80 are provided with indicia 82 adjacent to each respective lamp to indicate total user force applied. The plurality of lamps may illuminate up to and including the user force applied, or, alternatively, only one lamp 80 may be illuminated to indicate, by virtue of the adjacent indication 82 the total number of pounds of user force applied.

Figure 10:
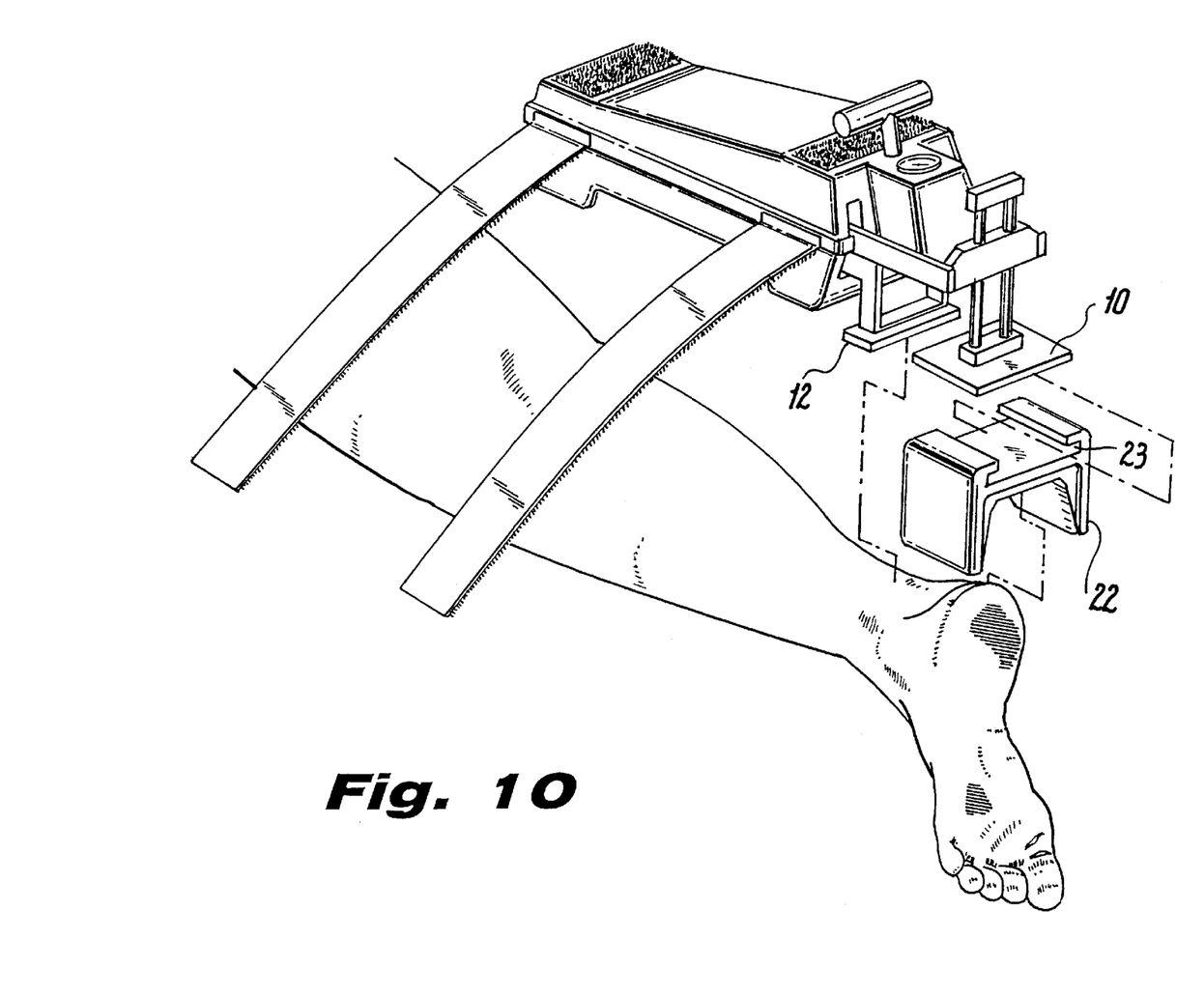
FIG. 10 shows an exploded view showing the Calcaneous reference pad of the prior art KT1000 in positional relationship to receptacle and in positional relationship to use of the present invention on the heel of a patient for measuring ankle joint laxity.

FIG. 10 shows an exploded view showing the Calcaneous reference pad 10 of the prior art KT1000 in positional relationship to attachment channels 23 of receptacle 22 and in positional relationship to use of the present invention on the heel of a patient for measuring ankle joint laxity.

Figure 11:
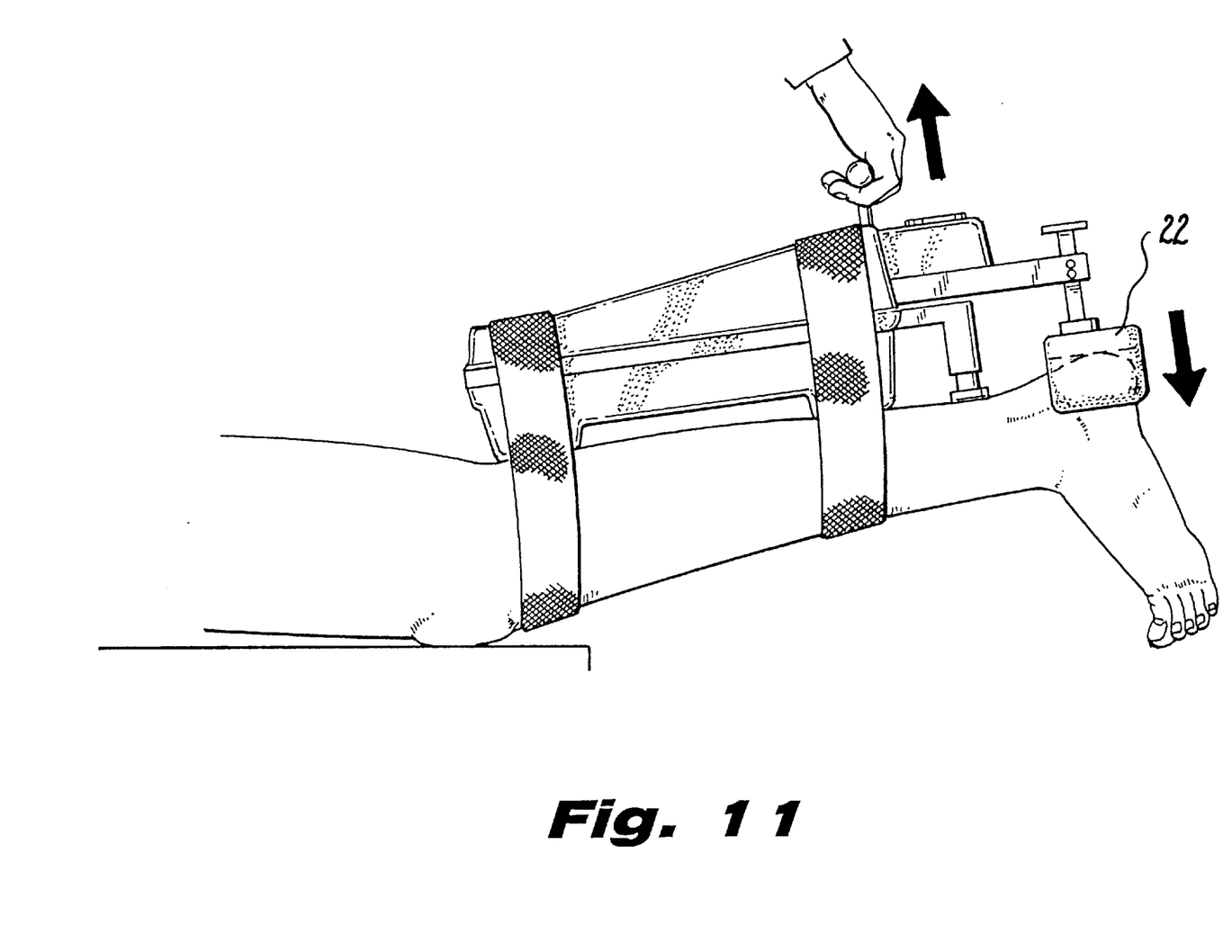
FIG. 11 shows a side elevation of the receptacle of the present invention installed on the prior art KT1000 and in position for use in measuring ankle joint laxity of a patient.

FIG. 11 shows a side elevation of the receptacle 22 of the present invention installed on the prior art KT1000 and in position for use in measuring ankle joint laxity of a patient.

Figure 12:
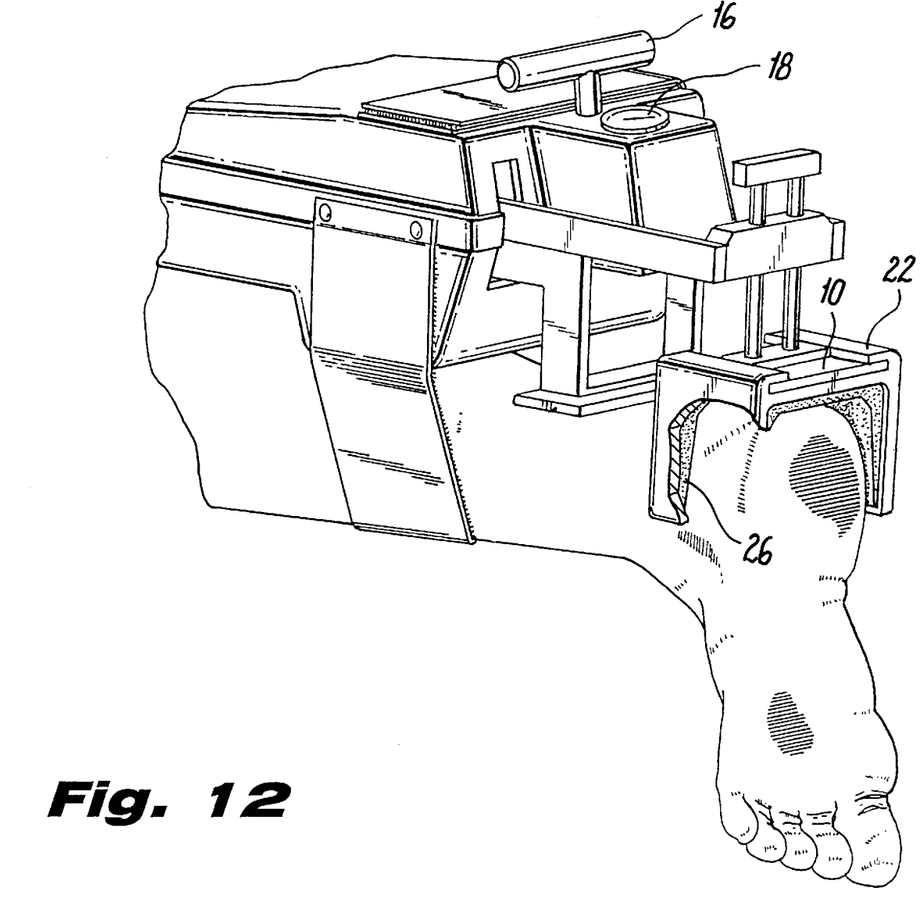
FIG. 12 shows a cutaway perspective view of the calcaneous receptacle of the present invention installed upon the prior art KT1000 and grasping the heel of a patient.

FIG. 12 shows a cutaway perspective view of the calcaneous receptacle 22 of the present invention installed upon the prior art KT1000 by sliding calcaneous pad 10 of the KT1000 into attachment channels 23 of receptacle 22. The cutaway view also shows non-slippery material 26 in contact with the and grasping the heel of a patient.

Figure 13:
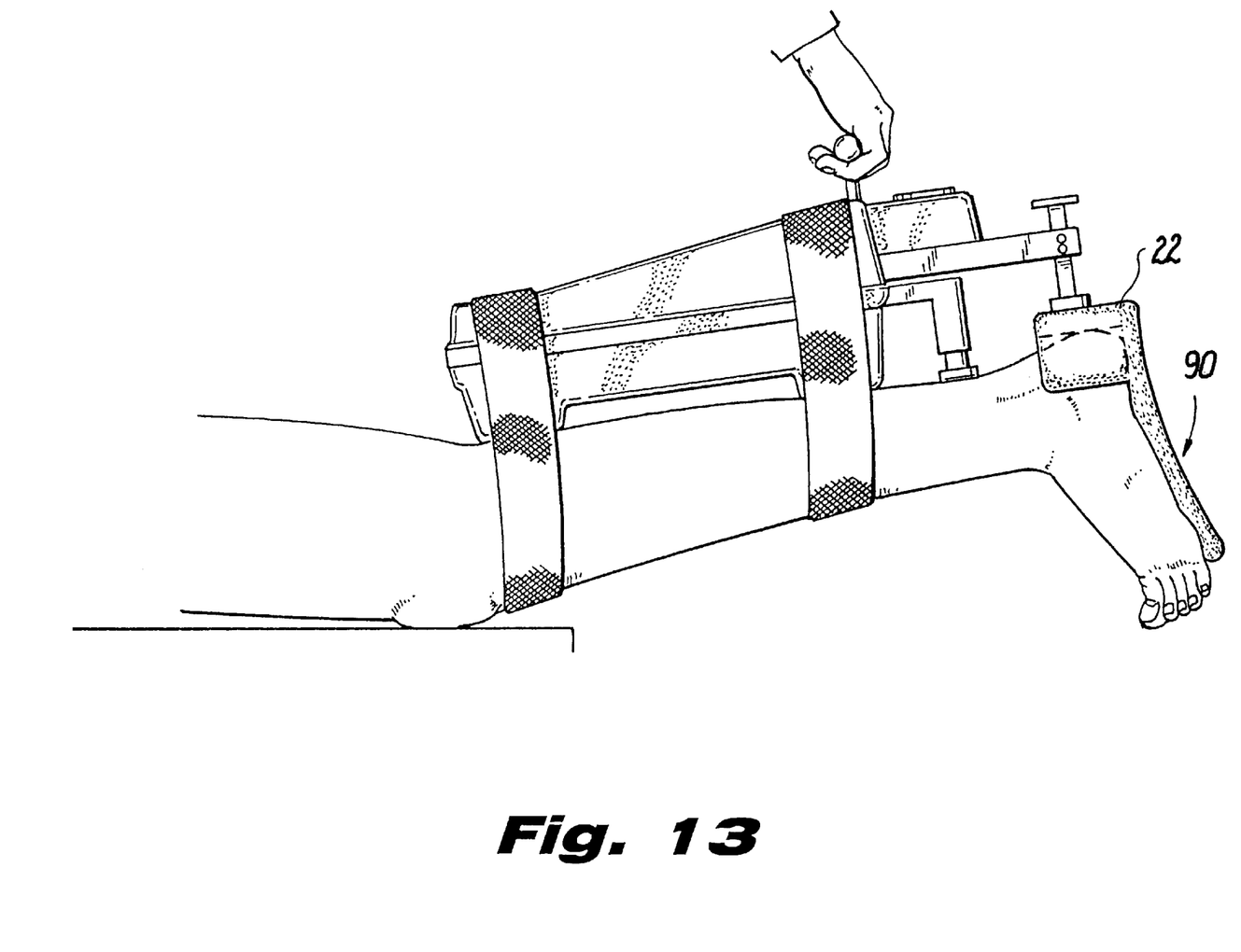
FIG. 13 shows a side elevation of the calcaneous receptacle of the present invention having a foot stop plate attached.

FIG. 13 shows a side elevation of calcaneous receptacle 22 having a foot stop plate 90 attached. Foot stop plate 90 is suitably attached to receptacle 22 so as to contact the plantar surface of the patient's foot, thereby conveniently and accurately positioning receptacle 22 upon the patient's heel.

What is claimed is:

1. An improved KT 1000™ device for measuring the anatomical joint laxity of a patient undergoing medical examination, comprising means for measuring relative movement in anatomical joints, and further comprising:

a. a pair of reference pads for contacting the anatomy of the patient whose joint laxity is to be measured, the reference pads being capable of moving relative to each other in response to relative force applied by the user; and wherein further b. the pair of reference pads is provided with indicator means for indicating the direction of travel of the pads relative to each other; and c. the pair of reference pads is further provided with indicator means for indicating the distance traveled by one pad relative to the other; and where d. the pair of reference pads is further provided with indicator means for indicating the amount of relative force applied to the pads; and e. the pair of reference pads being further provided with a downwardly extending receptacle for convenient and secure alignment and affixing to the heel therebelow of a patient lying in the prone position for measuring the laxity of joints; and wherein both the receptacle and the patient's ankle are free from exposure to weight bearing force other than that applied for purposes of joint laxity measurement;

f. the receptacle being adjustable by the user to secure the device in place on the patient's anatomy being measured.

2. The device of claim 1, further wherein:

a. the means for indicating the amount of relative force applied to the reference pads comprises visual indication means; and b. the indicator means for indicating the distance traveled by one pad relative to the other further comprises a maximum-reading indicator so as to indicate increasing relative distance traveled by the reference pads without resetting itself, the indicator requiring manual resetting for additional uses so as to relieve the user from the necessity of constant observation of the distance indicator; and further where c. the receptacle comprises a substantially concave shape.

3. The device of claim 2, further wherein the means for indicating the amount of relative force applied to the reference pads comprises a plurality of indicator lights sequentially illuminated in response to discrete incremental changes in force applied to the reference pads; and further the receptacle is provided with a pair of laterally adjustable clamping walls for grasping the anatomy of the patient to be examined;

the clamping walls further being provided with means to comfortably and conveniently adjust the device in a clamped position on the anatomy of the patient.

4. The device of claim 3 further wherein the receptacle clamping means further comprise threaded locking walls; and further wherein the receptacle comprises a suitable comfortable non-slippery material for grasping and clamping upon the anatomy of the patient being examined.

5. The device of claim 4 wherein the receptacle further comprises hinged attachment of the clamping walls to the receptacle, permitting the clamping walls to adjustably pivot in relation to the receptacle.

6. The device of claim 5 wherein further, the concave shape of the receptacle is comprised of a plurality of facets; and further where the receptacle further comprises a foot-stop plate for use in applying to the device to the foot of a patient adjacent to the calcaneous bone, when the device is used to measure the laxity of a patient's ankle joint.

7. The device of claim 6 wherein the receptacle comprises a discrete user-removable and user-installable adapter having means for convenient and suitable application to and removal from the reference pads.

8. The device of claim 7, further wherein the receptacle comprises a concave shape further comprising five facets for contacting the anatomy of the patient being examined; and wherein further the means for convenient and suitable application to and removal from the reference pads comprises a channel disposed on the receptacle for slidable friction-fitting on the reference pads.

9. The device of claim 8, further wherein the means for indicating the amount of relative force applied to the reference pads comprises a plurality of lights sequentially illuminated in response to discrete incremental changes in force applied to the reference pads, wherein further, each light sequentially illuminated represents 5 pounds of force applied to the reference pads.

10. The device of claim 8, further wherein the means for indicating the amount of lateral force applied to the reference pads comprises a plurality of lights sequentially illuminated in response to discrete incremental changes in force applied to the reference pads, wherein further, each light sequentially illuminated represents 3 pounds of force applied to the reference pads.

11. The device of claim 8, further wherein the means for indicating the amount of force applied to the reference pads comprises a plurality of indicator lights sequentially illuminated in response to discrete incremental changes in force applied to the reference pads, wherein further, the plurality of indicator lights is comprised of varying colors, with the illumination of each respective color and/or each respective combination of colors providing a coded indication of the amount of force.

12. The device of claim 8, further wherein the means for indicating the amount of force applied to the reference pads comprises a maximum-reading digital indicator requiring manual resetting; and further wherein the indicia of relative distance traveled by the reference pads comprises digital indicia.

13. A method of measuring the ankle joint laxity in a patient being medically examined, comprising the steps of:

a. affixing the device of claim 1 to the anatomy of the patient's foot, ankle and leg on the right or left side of the patient's body as required by the medical examination;

b. applying the reference pad comprising the receptacle to the patient's heel, the receptacle so affixed being a calcaneous receptacle; and c. applying the other reference pad by bringing it in contact with the posterior portion of the patient's calf, so that the reference pad is adjacent to and capable of pressing upon the patient's Achilles tendon, the reference pad so affixed being a tibial reference pad since in position it is disposed adjacent to the patient's tibial bone; and d. applying force to the reference pads so as to produce lateral movement therebetween;

e. observing and recording the indication of the amount of lateral distance traveled by the reference pads in relation to each other; and f. observing and recording the indication of the amount of force applied to the reference pads as indicated by the force indicia; and g. repeating the foregoing steps on the patient's other foot, ankle and leg for reference comparison; and h. repeating the foregoing sequence to observe and record inherent intra-patient variability.

14. The method of claim 13, further comprising performance of the steps using the device of claim 3.

15. The method of claim 14, further comprising performance of the steps using the device of claim 7.

16. The method of claim 15, further comprising performance of the steps using the device of claim 8.

17. The method of claim 16, further comprising performance of the steps using the device of claim 9.

18. The method of claim 17, further comprising performance of the steps using the device of claim 10.

19. The method of claim 18, further comprising performance of the steps using the device of claim 11.

20. The method of claim 19, further comprising performance of the steps using the device of claim 12.

21. An improved KT 1000™ device for measuring the anatomical joint laxity of a patient undergoing medical examination, comprising, in combination with the KT 1000™:

at least one receptacle having means for convenient and secure affixing to desired anatomical structures for measuring the laxity of joints; and wherein the at least one receptacle being attachable to and removable from the KT 1000™ by the user; and wherein further the at least one receptacle comprises means for secure and convenient attachment of the at least one receptacle to and removal of the at least one receptacle from the KT 1000™ ; and wherein further the at least one receptacle comprises a substantially concave shape; and the at least one receptacle comprises a pair of laterally adjustable clamping walls for grasping the anatomy of the patient to be examined; the clamping walls further being provided with means to comfortably and conveniently adjust the at least one receptacle in a clamped position on the anatomy of the patient.

22. The device of claim 21 further wherein the receptacle clamping walls further comprise threaded locking means; and further wherein the receptacle comprises a suitable comfortable non-slippery material for grasping and clamping upon the anatomy of the patient being examined.

23. The device of claim 22 wherein the at least one receptacle further comprises hinged attachment of the clamping walls to the at least one receptacle, permitting the clamping walls to adjustably pivot in relation to the receptacle.

24. The device of claim 23 wherein further, the concave shape of the receptacle is comprised of a plurality of facets;

and further where the receptacle further comprises a foot-stop plate for use in applying to the device to the foot of a patient adjacent to the calcaneous bone, when the device is used to measure the laxity of a patient's ankle joint.

25. The device of claim 24, further wherein the concave shape of the receptacle comprises five facets for contacting the anatomy of the patient being examined; and wherein the means for convenient and suitable application to and removal of the receptacle respectively to and from the KT 1000™ comprises a channel disposed on the receptacle for slidable friction-fitting on the KT 1000™.

26. A method of measuring the ankle joint laxity in a patient being medically examined, comprising the steps of:
   a. affixing the device of claim 21 to the anatomy of the patient's foot, ankle and leg;
   b. applying the at least one receptacle to the patient's heel, the receptacle so affixed comprising a calcaneous receptacle; and
   c. applying a KT 1000™ reference pad to the patient by bringing it in contact with the posterior portion of the patient's calf, so that the reference pad is adjacent to and capable of pressing upon the patient's Achilles tendon, the reference pad so affixed being a tibial reference pad since in position it is disposed adjacent to the patient's tibial bone; and
   d. applying force to the respective reference pad and the calcaneous receptacle so as to produce lateral movement therebetween;
   e. observing and recording the indication of the amount of lateral distance traveled by the reference pad and the calcaneous receptacle relative to each other; and
   f. observing and recording the indication of the amount of force applied to produce the relative distance traveled by the reference pad and calcaneous receptacle relative to each other as indicated by the force indicia; and
   g. repeating the foregoing steps on the patient's other foot, ankle and leg for reference comparison; and
   h. repeating the foregoing sequence to observe and record inherent intra-patient variability.

27. The method of claim 26, further comprising performance of the steps using the device of claim 22.

28. The method of claim 26, further comprising performance of the steps using the device of claim 23.

29. The method of claim 26, further comprising performance of the steps using the device of claim 24.

30. The method of claim 26, further comprising performance of the steps using the device of claim 25.

31. A method of measuring the ankle joint laxity in a patient being medically examined, comprising the steps of:
   a. affixing the KT 1000™ prior art device to the anatomy of the patient's foot, ankle and leg;
   b. applying one KT 1000™ reference pad to the patient's heel, the reference pad so affixed comprising a calcaneous reference pad; and
   c. applying a KT 1000™ reference pad to the patient by bringing it in contact with the posterior portion of the patient's calf, so that the reference pad is adjacent to and capable of pressing upon the patient's Achilles tendon, the reference pad so affixed being a tibial reference pad since in position it is disposed adjacent to the patient's tibial bone; and
   d. applying force to the respective calcaneous and tibial reference pads so as to produce lateral movement therebetween;
   e. observing and recording the indication of the amount of lateral distance traveled by the respective reference pads relative to each other; and
   f. observing and recording the indication of the amount of force applied to produce the relative distance traveled by the reference pads relative to each other as indicated by the KT 1000™ force indicia; and
   g. repeating the foregoing steps on the patient's other foot, ankle and leg for reference comparison; and
   h. repeating the foregoing sequence to observe and record inherent intra-patient variability.

* * * * *